United States Patent
Laszlo et al.

(10) Patent No.: US 11,636,349 B2
(45) Date of Patent: Apr. 25, 2023

(54) NEURAL FUNCTIONAL LOCALIZATION USING SYNAPTIC CONNECTIVITY GRAPHS

(71) Applicant: X Development LLC, Mountain View, CA (US)

(72) Inventors: Sarah Ann Laszlo, Mountain View, CA (US); Matthew Sibigtroth, Richmond, CA (US); Bin Ni, Fremont, CA (US)

(73) Assignee: X Development LLC, Mountain View, CA (US)

( * ) Notice: Subject to any disclaimer, the term of this patent is extended or adjusted under 35 U.S.C. 154(b) by 383 days.

(21) Appl. No.: 16/829,107

(22) Filed: Mar. 25, 2020

(65) Prior Publication Data

US 2021/0304011 A1   Sep. 30, 2021

(51) Int. Cl.
  *G06N 3/10*  (2006.01)
  *G06N 3/04*  (2006.01)
  *G06N 3/08*  (2006.01)

(52) U.S. Cl.
  CPC .............. *G06N 3/10* (2013.01); *G06N 3/04* (2013.01); *G06N 3/08* (2013.01)

(58) Field of Classification Search
  CPC ........ G16H 30/40; G16H 50/20; G16H 50/50; G06N 3/04; G06N 3/08; G06N 3/10; G06N 3/0454; A61B 5/7267; A61B 5/4064; A61B 5/0042
  See application file for complete search history.

(56) References Cited

U.S. PATENT DOCUMENTS

| | | | |
|---|---|---|---|
| 2019/0005384 A1* | 1/2019 | Sundar | G06N 3/04 |
| 2020/0293899 A1* | 9/2020 | Fernando | G06N 3/0454 |

OTHER PUBLICATIONS

Rosenthal, Gideon, et al. "Mapping higher-order relations between brain structure and function with embedded vector representations of connectomes." Nature communications 9.1 (2018): 1-12. (Year: 2018).*

(Continued)

*Primary Examiner* — Vu Le
*Assistant Examiner* — Tracy Mangialaschi
(74) *Attorney, Agent, or Firm* — Fish & Richardson P.C.

(57) ABSTRACT

Methods, systems, and apparatus, including computer programs encoded on a computer storage medium, for identifying one or more regions of a brain of a biological organism that are predicted to be functionally-specialized for performing a task. In one aspect, a method comprises: obtaining data defining a synaptic connectivity graph representing synaptic connectivity between neurons in the brain of the biological organism; identifying a plurality of sub-graphs of the synaptic connectivity graph; determining, for each sub-graph of the plurality of sub-graphs, a performance measure characterizing a performance of a neural network having a neural network architecture that is specified by the sub-graph in accomplishing the task; and determining, based on the performance measures, that one or more sub-graphs of the plurality of sub-graphs correspond to regions of the brain of the biological organism that are predicted to be functionally-specialized for performing the task.

20 Claims, 4 Drawing Sheets

(56) References Cited

OTHER PUBLICATIONS

Suárez LE, Markello RD, Betzel RF, Misic B. Linking structure and function in macroscale brain networks. Trends in Cognitive Sciences. Feb. 24, 2020;24(4):302-315. (Year: 2020).*

Li, Yang, et al. "Mapping brain structural connectivities to functional networks via graph encoder-decoder with interpretable latent embeddings." 2019 IEEE Global Conference on Signal and Information Processing (GlobalSIP). IEEE, 2019. (Year: 2019).*

Brown CJ, Hamarneh G. Machine learning on human connectome data from MRI. arXiv preprint arXiv:1611.08699. Nov. 26, 2016. (Year: 2016).*

PCT International Search Report and Written Opinion in International Appln. No. PCT/US2020/066521, dated Mar. 25, 2020, 16 pages.

Rosenthal et al., "Mapping higher-order relations between brain structure and function with embedded vector representations of connectomes," Nature Communications, Dec. 2018, 9 (1):12 pages.

Suarez et al., "Linking Structure and Function in Macroscale Brain Networks," Trends in Cognitive Sciences, Apr. 2020, 24(4):302-315.

Golovin et al, "Google vizier: A service for black-box optimization," In Proceedings of the 23rd ACM SIGKDD International Conference on Knowledge Discovery and Data Mining, 2017, 10 pages.

Kim et al, "Information-rich Localization Microscopy Through Machine Learning," Nature Communications, Apr. 30, 2019, 8 pages.

Li et al, "Brain Biomarker Interpretation in ASD Using Deep Learning and fMRI," arXiv, Aug. 23, 2018, 8 pages.

Salehi et al, "An exemplar-based Approach to Individualized Parcellation Reveals the Need for Sex Specific Functional Networks," Elsevier, Sep. 5, 2017, 14 pages.

Seguin et al, "Inferring neural signalling directionality from undirected structure connectomes," Nature Communications, Sep. 19, 2019.

Swallow et al, "Reliability of Functional Localization Using fMRI," Washington University, Jul. 14, 2003, 17 pages.

International Preliminary Report on Patentability in International Appln. No. PCT/US2020/066521, dated Oct. 6, 2022, 10 pages.

\* cited by examiner

NEURAL FUNCTIONAL LOCALIZATION USING SYNAPTIC CONNECTIVITY GRAPHS

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that performs neural functional localization, i.e., by identifying regions of the brain of a biological organism that are functionally-specialized for performing a task. The task may be, e.g., a visual or auditory data processing task. The system obtains a synaptic connectivity graph representing synaptic connectivity between neurons in the brain, identifies multiple sub-graphs of the synaptic connectivity graph, and instantiates a respective artificial neural network corresponding to each sub-graph. The artificial neural network corresponding to a sub-graph has an architecture that is specified by the sub-graph. The system trains the artificial neural networks corresponding to the sub-graphs to perform the task and identifies one or more best-performing artificial neural network architectures. The system then identifies the brain regions associated with the sub-graphs specifying the best-performing architectures as being functionally-specialized for performing the task in the brain of the biological organism.

According to a first aspect, there is provided a method performed by one or more data processing apparatus for identifying one or more regions of a brain of a biological organism that are predicted to be functionally-specialized for performing a task, the method comprising: obtaining data defining a synaptic connectivity graph representing synaptic connectivity between neurons in the brain of the biological organism; identifying a plurality of sub-graphs of the synaptic connectivity graph; determining, for each sub-graph of the plurality of sub-graphs, a performance measure characterizing a performance of a neural network having a neural network architecture that is specified by the sub-graph in accomplishing the task; and determining, based on the performance measures, that one or more sub-graphs of the plurality of sub-graphs correspond to regions of the brain of the biological organism that are predicted to be functionally-specialized for performing the task.

In some implementations, the synaptic connectivity graph comprises a plurality of nodes and edges, wherein each edge connects a pair of nodes, each node corresponds to a respective neuron in the brain of the biological organism, and each edge connecting a pair of nodes in the synaptic connectivity graph corresponds to a synaptic connection between a pair of neurons in the brain of the biological organism.

In some implementations, the method further comprises determining the neural network architecture that is specified by each sub-graph, comprising, for each sub-graph: mapping each node in the sub-graph to a corresponding artificial neuron in the neural network architecture; and for each edge in the sub-graph: mapping the edge to a connection between a pair of artificial neurons in the neural network architecture that correspond to the pair of nodes in the sub-graph that are connected by the edge.

In some implementations, wherein identifying the plurality of sub-graphs of the synaptic connectivity graph comprises, at each of a plurality of iterations: identifying a current sub-graph of the synaptic connectivity graph in accordance with current values of one or more parameters; and updating the current values of the parameters based at least in part on the performance measure characterizing the performance of the neural network having the neural network architecture that is specified by the current sub-graph in accomplishing the task.

In some implementations, determining, for each sub-graph of the plurality of sub-graphs, a performance measure characterizing a performance of a neural network having a neural network architecture that is specified by the sub-graph in accomplishing the task comprises, for each sub-graph: training the neural network having the neural network architecture that is specified by the sub-graph to accomplish the task; and evaluating the performance of the trained neural network having the neural network architecture that is specified by the sub-graph in accomplishing the task.

In some implementations, evaluating the performance of the trained neural network having the neural network architecture that is specified by the sub-graph in accomplishing the task comprises: determining an accuracy of the trained neural network having the neural network architecture in accomplishing the task.

In some implementations, evaluating the performance of the trained neural network having the neural network architecture that is specified by the sub-graph in accomplishing the task further comprises: determining a measure of complexity of the neural network architecture that is specified by the sub-graph.

In some implementations, the method further comprises: providing data identifying the one or more sub-graphs of the plurality of sub-graphs corresponding to regions of the brain of the biological organism that are predicted to be functionally-specialized for performing the task.

In some implementations, the method further comprises: generating a visualization of the one or more sub-graphs of the plurality of sub-graphs corresponding to regions of the brain of the biological organism that are predicted to be functionally-specialized for performing the task.

In some implementations, the task is a visual data processing task.

In some implementations, the task is an audio data processing task.

In some implementations, obtaining data defining the synaptic connectivity graph representing synaptic connectivity between neurons in the brain of the biological organism comprises: obtaining a synaptic resolution image of at least a portion of the brain of the biological organism; and processing the image to identify: (i) a plurality of neurons in the brain, and (ii) a plurality of synaptic connections between pairs of neurons in the brain.

In some implementations, the synaptic resolution image of the brain of the biological organism is generated using electron microscopy techniques.

In some implementations, determining, based on the performance measures, that one or more sub-graphs of the plurality of sub-graphs correspond to regions of the brain of the biological organism that are predicted to be functionally-specialized for performing the task comprises: determining that a sub-graph associated with a highest performance measure corresponds to a region of the brain that is predicted to be functionally-specialized for performing the task.

According to a second aspect there is provided a system comprising one or more computers and one or more storage devices communicatively coupled to the one or more computers, wherein the one or more storage devices store instructions that, when executed by the one or more computers, cause the one or more computers to perform operations comprising the method of the first aspect.

According to a third aspect there are provided one or more non-transitory computer storage media storing instructions that when executed by one or more computers cause the one or more computers to perform operations comprising the method of the first aspect.

Particular embodiments of the subject matter described in this specification can be implemented so as to realize one or more of the following advantages.

The functional localization system described in this specification can perform synaptic resolution functional localization, i.e., by identifying regions of a brain at synaptic resolution that are predicted to be functionally-specialized for performing a task. In contrast, some other functional localization techniques, e.g., using functional magnetic resonance imaging, may localize brain regions at a substantially lower resolution, e.g., at millimeter resolution rather than at synaptic resolution. Performing functional localization at synaptic resolution facilitates more detailed analysis and visualization of functionally-specialized brain regions. For example, the functional localization system may be used to quantitatively characterize changes in functionally localized regions of the brain of a patient over time (e.g., as a result of administration of a drug) at synaptic resolution, as will be described in more detail below.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
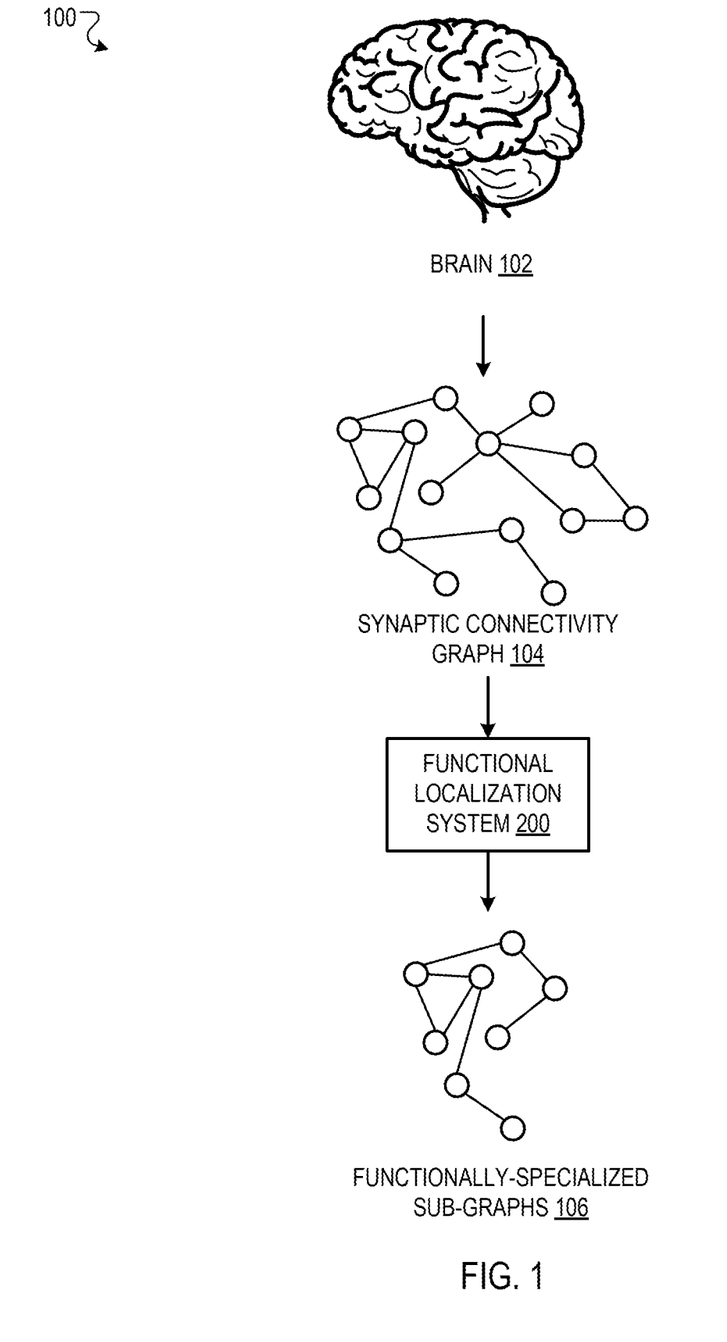
FIG. 1 shows an example data flow for performing neural functional localization by identifying regions of a brain of a biological organism that are functionally-specialized for performing a task in the brain.

FIG. 1 shows an example data flow 100 for performing neural functional localization by identifying regions of a brain 102 of a biological organism that are functionally-specialized for performing a task in the brain. The task may be, e.g., a visual data processing task, an audio data processing task, a language processing task, a motor control task, or a combination thereof.

As used throughout this document, a brain may refer to any amount of nervous tissue from a nervous system of a biological organism, and nervous tissue may refer to any tissue that includes neurons (i.e., nerve cells). The biological organism may be, e.g., a worm, a fly, a mouse, a cat, or a human. A region of the brain refers to a collection of neurons in the brain. A brain region may be referred to as being functionally-specialized for performing a task if the operations of the neurons in the region are closely associated with the task being performed in the brain, e.g., such that disrupting or damaging the region may diminish the capacity of the brain to perform the task.

The functional localization system 200 is configured to perform neural functional localization by processing a synaptic connectivity graph 104 representing synaptic connectivity between neurons in the brain to output data specifying one or more functionally-specialized sub-graphs 106 of the synaptic connectivity graph 104. The functional localization system 200 is described in more detail with reference to FIG. 2.

The synaptic connectivity graph 104 is a graph defined by a set of nodes and edges, where each edge connects a pair of nodes. Each node in the synaptic connectivity graph 104 corresponds to a respective neuron in the brain 102, and two nodes in the graph 104 are connected if the corresponding neurons in the brain 102 share a synaptic connection. A functionally-specialized sub-graph 106 refers to a sub-graph of the synaptic connectivity graph 104 specifying a region of the brain 102 that is predicted to be functionally-specialized for performing a task. A sub-graph of the synaptic connectivity graph 104 may refer to a graph specified by a proper subset of the nodes and edges of the synaptic connectivity graph 104.

The functionally-specialized sub-graphs 106 generated by the functional localization system 200 can be used for any of a variety of purposes. A few example use cases for the functionally-specialized sub-graphs 106 are described in more detail next.

In one example, the functionally-specialized sub-graphs 106 may be processed to generate a two- or three-dimensional geometric visualization of the corresponding functionally-specialized brain regions. The visualization may visually distinguish the functionally-specialized brain regions at synaptic resolution, e.g., by visually distinguishing the individual neurons and synapses specified by the functionally-specialized sub-graphs. The neurons and synapses of the functionally-specialized brain regions may be visually distinguished in any appropriate manner, e.g., by being colored in a manner that visually distinguishes them from the remainder of the brain. The visualization of the functionally-specialized brain regions may be used, e.g., to facilitate medical procedures such as brain surgery. For example, a physician performing brain surgery may use the visualization to minimize damage to functionally-specialized brain regions.

In another example, the functionally-specialized sub-graphs 106 may be used to quantitatively characterize changes in the brain of a patient over time. For example, the functional localization system 200 may identify respective functionally-specialized sub-graphs of the brain 102 at multiple time points, e.g., before and after a drug is administered to the patient. Features characterizing the functionally-specialized sub-graphs 106 may be generated and thereafter used to characterize temporal changes in the brain that may be relevant to medical decisions, e.g., regarding whether a treatment affecting the brain should be discontinued. The features characterizing a functionally-specialized sub-graph 106 may include, e.g., a feature specifying the average number of edges connected to each node in the sub-graph, the number of nodes in the sub-graph, or both.

The synaptic connectivity graph 104 representing synaptic connectivity between neurons in the brain 102 may be generated in any of a variety of ways. For example, a graphing system may generate the synaptic connectivity graph 104 by obtaining a synaptic resolution image of the brain (a "brain image") and processing the brain image to identify the neurons and synapses depicted in the brain image.

The graphing system may further identify a weight value associated with each edge in the synaptic connectivity graph 104. For example, the graphing system may identify a weight for an edge connecting two nodes in the synaptic connectivity graph 104 based on an area of overlap between tolerance regions around the respective neurons corresponding to the nodes in the brain image. The area of overlap may be measured, e.g., as the number of voxels in the brain image that are contained in the overlap of the respective tolerance regions around the neurons. A "tolerance region" around a neuron refers to a contiguous region of the brain image that includes the neuron. For example, the tolerance region around a neuron may be specified as the set of spatial locations in the brain image that are either: (i) in the interior of the neuron, or (ii) within a predefined distance of the interior of the neuron. The weight for an edge connecting two nodes in the synaptic connectivity graph 104 may be understood as characterizing the (approximate) strength of the connection between the corresponding neurons in the brain (e.g., the amount of information flow through the synapse connecting the two neurons).

In addition to identifying synapses in the brain image, the graphing system may further determine the direction of each synapse using any appropriate technique. The "direction" of a synapse between two neurons refers to the direction of information flow between the two neurons, e.g., if a first neuron uses a synapse to transmit signals to a second neuron, then the direction of the synapse would point from the first neuron to the second neuron. Example techniques for determining the directions of synapses connecting pairs of neurons are described with reference to: C. Seguin, A. Razi, and A. Zalesky: "Inferring neural signalling directionality from undirected structure connectomes," Nature Communications 10, 4289 (2019), doi:10.1038/s41467-019-12201-w.

In implementations where the graphing system determines the directions of the synapses in the brain image, the graphing system may associate each edge in the graph with direction of the corresponding synapse. That is, the synaptic connectivity graph may be a directed graph. In other implementations, the synaptic connectivity graph may be an undirected graph, i.e., where the edges in the graph are not associated with a direction.

The synaptic connectivity graph 104 may be represented in any of a variety of ways, e.g., by an adjacency matrix. The adjacency matrix may be represented as a two-dimensional array of numerical values with a number of rows and columns equal to the number of nodes in the graph. The component of the array at position (i,j) may have value 1 if the graph includes an edge pointing from node i to node j, and value 0 otherwise.

An example process for generating a synaptic connectivity graph from a brain image is described in more detail with reference to U.S. patent application Ser. No. 16/776,108, which is hereby incorporated by reference. For example, the graphing system described with reference to FIG. 2 of U.S. patent application Ser. No. 16/776,108 provides one example of a system for generating a synaptic connectivity graph from a brain image.

Figure 2:
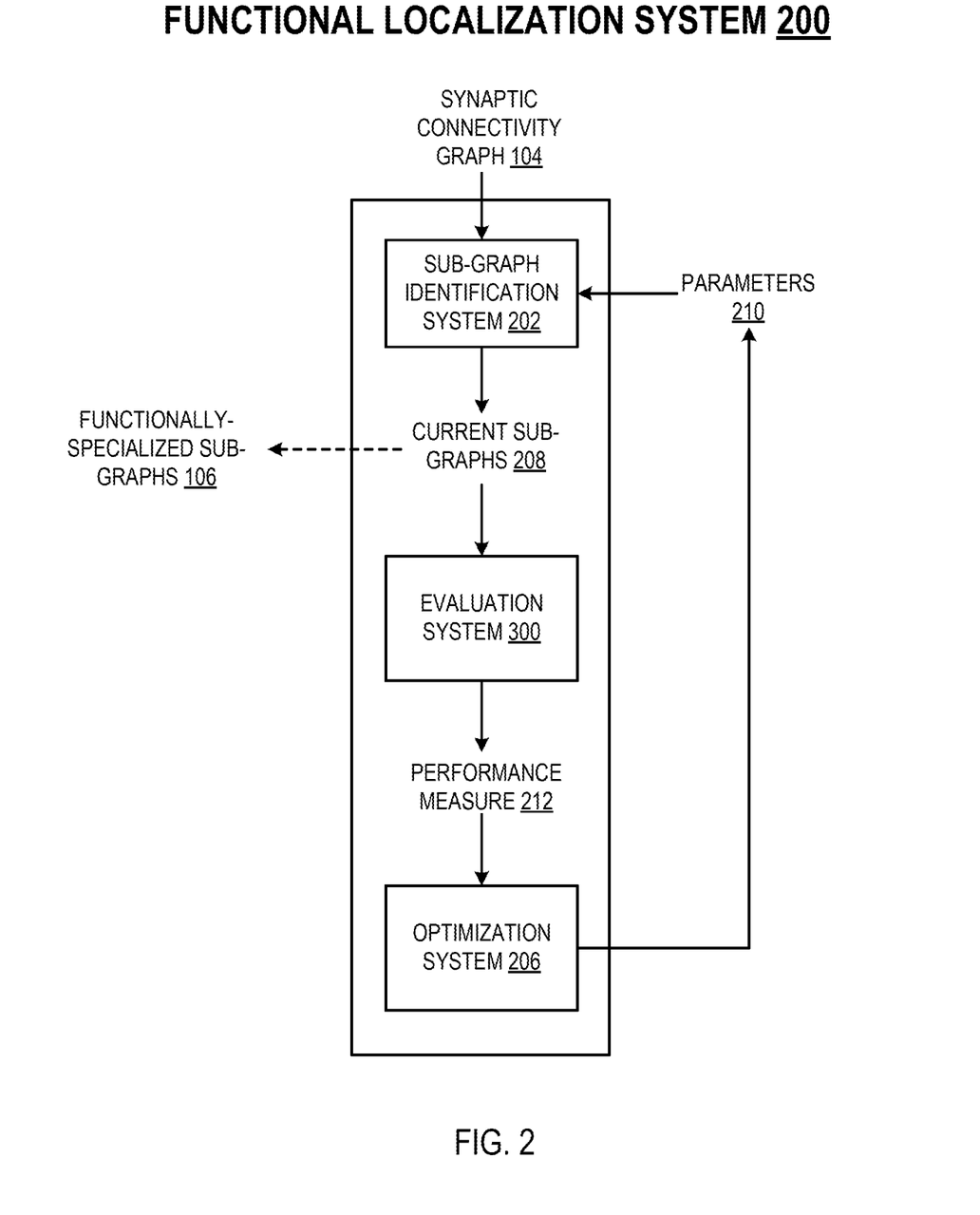
FIG. 2 is a block diagram of an example functional localization system.

FIG. 2 is a block diagram of an example functional localization system 200. The functional localization system 200 is an example of a system implemented as computer programs on one or more computers in one or more locations in which the systems, components, and techniques described below are implemented.

The functional localization system 200 is configured to perform neural functional localization by processing a synaptic connectivity graph 104 representing synaptic connectivity in a brain to output data specifying one or more functionally-specialized sub-graphs 106 of the synaptic connectivity graph 104. Each functionally-specialized sub-graph 106 corresponds to a region of the brain that is predicted to be functionally-specialized for performing a task.

The functional localization system 200 includes a sub-graph identification system 202, an evaluation system 300, and an optimization system 206, which will each be described in more detail next.

At each of multiple iterations, the sub-graph identification system 202 identifies one or more current sub-graphs 208 of the synaptic connectivity graph 104 in accordance with current values of a set of parameters 210 of the sub-graph identification system 202. For example, to identify the current sub-graphs 208, the sub-graph identification system 202 may identify one or more regions of the adjacency matrix representing the synaptic connectivity graph 104 in accordance with the current values of the parameters 210. A "region" of the adjacency matrix refers to a subset of the components (i.e., entries) of the adjacency matrix, e.g., a sub-matrix of the adjacency matrix that is specified by a square or rectangular block of components from the adjacency matrix. Each of the identified regions of the adjacency matrix of the synaptic connectivity graph 104 may define a corresponding current sub-graph 208. In particular, each region of the adjacency matrix specifies a subset of the edges of the synaptic connectivity graph 104, and the corresponding current sub-graph 208 may be defined by: (i) the specified subset of the edges of the synaptic connectivity graph 104, and (ii) the subset of nodes of the synaptic connectivity graph 104 that are connected by the specified subset of the edges.

At each iteration, the evaluation system 300 determines a respective performance measure 212 associated with each current sub-graph 208. Generally, the performance measure 212 for a sub-graph 208 characterizes the performance of an artificial neural network having a neural network architecture that is specified by the sub-graph 208 in accomplishing the task. An example evaluation system 300 is described in more detail with reference to FIG. 3.

At each iteration, the optimization system 206 updates the current values of the parameters 210 based on the performance measures 212 associated with the current sub-graphs 208. In particular, the optimization system 206 may update the current values of the parameters 210 to encourage the generation of sub-graphs 208 with higher (i.e., superior) performance measures 212. Prior to the first iteration, the values of the parameters 210 may be initialized to default values or random values.

A few example implementations of the sub-graph identification system 202 and the optimization system 206 are described in more detail next.

In some implementations, the parameters 210 of the sub-graph identification system 202 specify a region of the adjacency matrix representing the synaptic connectivity graph 104, and at each iteration, the sub-graph identification system 202 outputs a current sub-graph 208 defined by the specified region of the adjacency matrix. At each iteration, the evaluation system 300 determines the performance measure 212 for the current sub-graph 208, and the optimization system 206 updates the current values of the parameters 210 to optimize the performance measures 212 using a "black-box" optimization technique. A black-box optimization technique may refer to a technique for optimizing a function that does not rely on an analytical or closed-form expression of the function, i.e., that can treat the function as a black-box. In the current context, the optimization system 206 may use a black-box optimization technique to optimize the function defined by the mapping from the parameters 210 of the sub-graph identification system 202 to the corresponding performance measures 212 generated by the evaluation system 300. Examples of black-box optimization techniques which may be implemented by the optimization system 206 are described with reference to: Golovin, D., Solnik, B., Moitra, S., Kochanski, G., Karro, J., & Sculley, D.: "Google vizier: A service for black-box optimization," In Proceedings of the 23rd ACM SIGKDD International Conference on Knowledge Discovery and Data Mining, pp. 1487-1495 (2017).

In some implementations, the parameters 210 of the sub-graph identification system 202 specify a region of the adjacency matrix representing the synaptic connectivity graph 104, and at each iteration, the sub-graph identification system 202 outputs a respective current sub-graph 208 corresponding to each of multiple sub-regions of the specified region. For example, the parameters 210 of the sub-graph identification system 202 may specify a square region of the adjacency matrix, and the sub-graph identification system 202 may output a respective current sub-graph 208 corresponding to each quadrant of the square region of the adjacency matrix. The current sub-graph 208 corresponding to a quadrant of the square region of the adjacency matrix may be defined by a fixed-size sub-matrix located in the center of quadrant. At each iteration, the evaluation system 300 determines a respective performance measure 212 for the current sub-graph 208 corresponding to each sub-region, and the optimization system 206 updates the current values of the parameters 210 based on the performance measures 212. For example, the optimization system 206 may update the current values of the parameters 210 to specify the sub-region with the highest corresponding performance measure 212.

Generally, the parameters 210 of the sub-graph identification system 202 may specify a region of the adjacency matrix representing the synaptic connectivity graph 104 in any of a variety of ways. In one example, the parameters 210 of the sub-graph identification system 202 may include the coordinates of the vertices of a region of the adjacency matrix. In another example, the parameters 210 of the sub-graph identification system 202 may include the coordinates of the center of a square region of the adjacency matrix and parameters specifying the side-length of the square region of the adjacency matrix.

The functional localization system 200 may determine that a termination criterion is satisfied, e.g., after the parameters 210 of the sub-graph identification system 202 have been updated a predetermined number of times. The functional localization system 200 may thereafter identify one or more generated sub-graphs 208 as being functionally-specialized sub-graphs 106. For example, the functional localization system 200 may identify a predefined number of the generated sub-graphs 208 with the highest performance measures 212 as being functionally-specialized sub-graphs.

Figure 3:
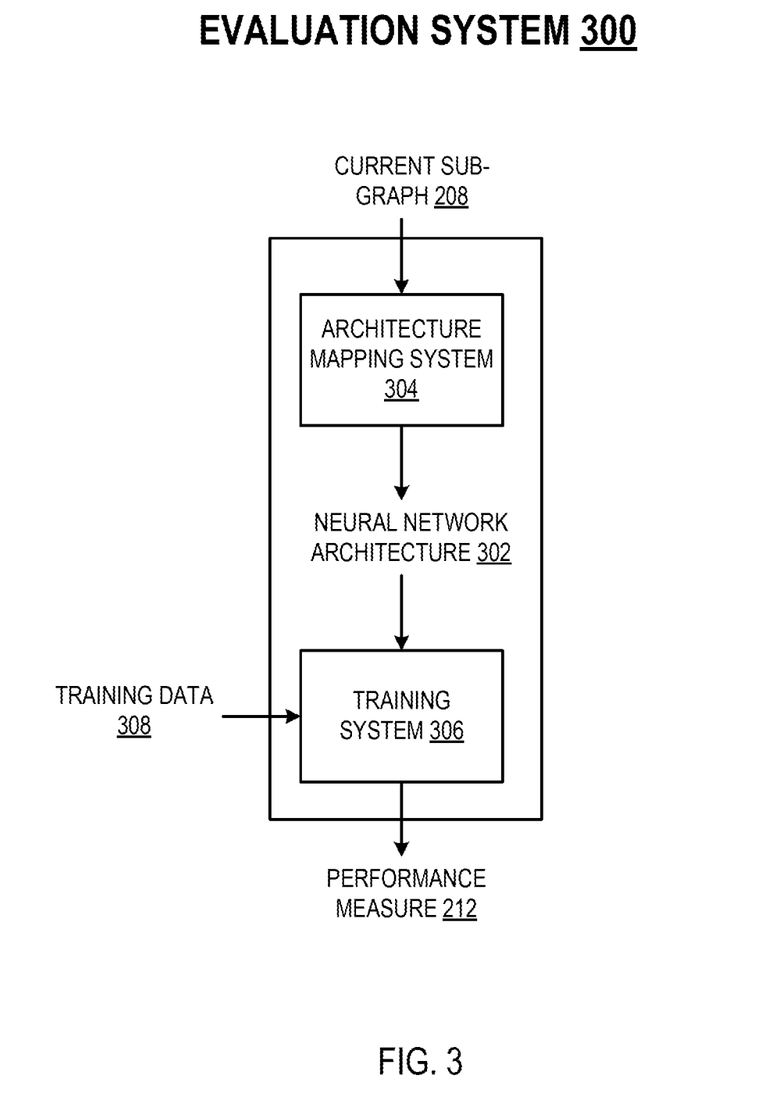
FIG. 3 is a block diagram of an example evaluation system.

FIG. 3 is a block diagram of an example evaluation system 300. The evaluation system 300 is an example of a system implemented as computer programs on one or more computers in one or more locations in which the systems, components, and techniques described below are implemented.

The evaluation system 300 is configured to process a current sub-graph 208 of a synaptic connectivity graph representing synaptic connectivity in a brain to generate a corresponding performance measure 212. The performance measure 212 characterizes the performance of an artificial neural network having a neural network architecture 302 that is specified by the current sub-graph 208 in accomplishing a task.

The evaluation system 300 includes an architecture mapping system 304 and a training system 306, which will each be described in more detail next.

The architecture mapping system 304 maps the current sub-graph 208 to a corresponding artificial neural network architecture 302. For example, the architecture mapping system 304 may map each node in the current sub-graph 208 to a corresponding artificial neuron in the neural network architecture 302, and map each edge in the current sub-graph 208 to a connection between a pair of artificial neurons in the neural network architecture 302. In particular, the architecture mapping system 304 may map each edge in the current sub-graph 208 to a connection between a pair of artificial neurons in the neural network architecture 302 that correspond to the pair of nodes in the current sub-graph 208 that are connected by the edge. The neural network architecture 302 may include: (i) a respective artificial neuron corresponding to each node in the current sub-graph 208, and (ii) a respective connection corresponding to each edge in the current sub-graph 208.

In some implementations, the current sub-graph 208 may be a directed graph, and an edge that points from a first node to a second node in the current sub-graph 208 may specify a connection pointing from a corresponding first artificial neuron to a corresponding second artificial neuron in the architecture 302. The connection pointing from the first artificial neuron to the second artificial neuron may indicate that the output of the first artificial neuron should be provided as an input to the second artificial neuron. Each connection in the architecture 302 may be associated with a weight value, e.g., that is specified by the weight value associated with the corresponding edge in the sub-graph.

An artificial neuron may refer to a component of the architecture 302 that is configured to receive one or more inputs (e.g., from one or more other artificial neurons), and to process the inputs to generate an output. The inputs to an artificial neuron and the output generated by the artificial neuron may be represented as scalar numerical values. In one example, a given artificial neuron may generate an output b as:

$$b = \sigma\left(\sum_{i=1}^{n} w_i \cdot a_i\right) \quad (1)$$

where σ(•) is a non-linear "activation" function (e.g., a sigmoid function or an arctangent function), $\{a_i\}_{i=1}^n$ are the inputs provided to the given artificial neuron, and $\{w_i\}_{i=1}^n$ are the weight values associated with the connections between the given artificial neuron and each of the other artificial neurons that provide an input to the given artificial neuron.

In some implementations, the current sub-graph 208 may be an undirected graph, and the architecture mapping system 304 may map an edge that connects a first node to a second node in the current sub-graph 208 to two connections between a corresponding first artificial neuron and a corresponding second artificial neuron in the architecture. In particular, the architecture mapping system 304 may map the edge to: (i) a first connection pointing from the first artificial neuron to the second artificial neuron, and (ii) a second connection pointing from the second artificial neuron to the first artificial neuron.

In some implementations, the current sub-graph 208 may be an undirected graph, and the architecture mapping system 304 may map an edge that connects a first node to a second node in the current sub-graph 208 to one connection between a corresponding first artificial neuron and a corresponding second artificial neuron in the architecture. The architecture mapping system 304 may determine the direction of the connection between the first artificial neuron and the second artificial neuron, e.g., by randomly sampling the direction in accordance with a probability distribution over the set of two possible directions.

Optionally, the architecture 302 may include artificial neurons and connections in addition to the artificial neurons and connections corresponding to the nodes and edges of the current sub-graph 208. For example, the architecture 302 specified by the current sub-graph 208 may include: (i) a "brain emulation" sub-network that includes artificial neurons and connections corresponding to the nodes and edges of the current sub-graph 208, and (ii) a "prediction" sub-network that includes additional artificial neurons and connections. In this example, a neural network having the architecture 302 may be configured to process an input using the brain emulation sub-network to generate an alternative representation of the input, and then process the alternative representation of the input using the prediction sub-network to generate an output. The architecture of the prediction sub-network may be less complex (e.g., have fewer parameters) than the architecture of the brain emulation sub-network. In particular examples, the prediction sub-network may include one, two, or three fully-connected layers.

The training system 306 trains a neural network having the architecture 302 specified by the current sub-graph 208 to accomplish a task. The task may be, e.g., a visual data processing task, an audio data processing task, a language processing task, a motor control task, or a combination thereof.

Generally, the training system 306 trains the neural network to perform the task by training the neural network on a set of training data 308 that is relevant to the task. The training data 308 includes multiple training examples, where each training example may specify: (i) a training input to the neural network, and (ii) a target output that should be generated by the neural network by processing the training input. Training the neural network on the training data 308 may include iteratively adjusting the parameters of the neural network to optimize an objective function that characterizes a measure of similarity between: (i) the outputs generated by the neural network, and (ii) the corresponding target outputs specified by the training examples. The objective function may be, e.g., a cross-entropy objective function or a squared-error objective function. The training system 306 may train the neural network using any appropriate machine learning training technique, e.g., stochastic gradient descent. A few examples of training a neural network to perform certain tasks are described in more detail next.

In one example, the training system 306 trains the neural network to perform a visual data processing task by processing an image to generate a classification of the image, e.g., that indicates a type of object depicted in the image.

In another example, the training system 306 trains the neural network to perform an audio data processing task by processing audio data to generate a classification of a phoneme or grapheme expressed in the audio data.

In another example, the training system 306 trains the neural network to perform a language processing task by processing an input sequence of text in a first natural language to generate a translation of the input sequence of text into a second natural language.

In another example, the training system 306 trains the neural network to perform a motor control task by processing an observation of an environment (e.g., an image of a real-world environment) to generate an action to be performed by an agent (e.g., a robotic agent) in response to the observation.

In some implementations, as described above, the neural network may include: (i) a brain emulation sub-network that includes artificial neurons and connections corresponding to the nodes and edges of the current sub-graph 208, and (ii) a prediction sub-network that includes additional artificial neurons and connections. In these implementations, rather than training the entire neural network from end-to-end, the training system 306 may be configured to train only the parameters of the prediction sub-network, while leaving the parameters of the brain emulation neural network fixed during training. That is, the training system 306 may treat the brain emulation sub-network as a static "reservoir" that generates informative representations of network inputs that are subsequently processed by the prediction sub-network to generate outputs. The parameter values of the brain emulation neural network (e.g., weight values associated with the connections between artificial neurons) may be determined before training, e.g., based on the weight values of the edges in the synaptic connectivity graph, as described above.

Training the neural network specified by the current sub-graph 208 from end-to-end (i.e., training both the parameters of the brain emulation sub-network and the parameters of the prediction sub-network) may be difficult due to the complexity of the architecture of the brain emulation sub-network. In particular, the brain emulation sub-network may have a very large number of trainable parameters and a highly recurrent architecture. Therefore, training the neural network specified by the current sub-graph 208 from end-to-end using machine learning training techniques may be computationally-intensive and the training may fail to converge, e.g., if the values of the parameters of the neural network oscillate rather than converging to fixed values. Even in cases where the training of the neural network converges, the performance of the neural network (e.g., measured by prediction accuracy) may fail to achieve an acceptable threshold. For example, the large number of parameters of the neural network may overfit the limited amount of training data. Training only the prediction sub-network while treating the brain emulation sub-network as a static reservoir enables the prediction sub-network to take advantage of the highly complex and non-linear behavior of the brain emulation sub-network in performing tasks while obviating the challenges of training the brain emulation sub-network.

The training system 306 may determine that the training of the neural network having the architecture 302 specified by the current sub-graph 208 is complete when a termination criterion is satisfied, e.g., when a predefined number of training iterations have been performed.

The training system 306 may determine the performance measure 212 corresponding to the current sub-graph 208 by evaluating the performance of the trained neural network having the architecture 302 on a set of test data. The test data includes multiple training examples that were not used during training of the neural network. The training system 306 may evaluate the performance of the trained neural network on the test data by evaluating a prediction accuracy of the trained neural network on the test data, e.g., using a cross-entropy objective function.

In some cases, training system 306 may additionally determine the performance measure 212 corresponding to the current sub-graph 208 based on a measure of complexity of the architecture 302 specified by the current sub-graph 208. The training system 306 may determine the measure of complexity of the architecture 302 based on, e.g., the number of arithmetic operations that are performed by a neural network having the architecture 302 in processing an input to generate an output. The training system 306 may determine the overall performance measure 212, e.g., a weight linear combination of: (i) the prediction accuracy, evaluated on the test data, of the trained neural network having the architecture 302, and (ii) the complexity of the architecture 302. Determining the performance measure 212 based on both the prediction accuracy and complexity associated with the architecture 302 may facilitate the identification of functionally-specialized sub-graphs (as described with reference to FIG. 2) that can perform a task both accurately and efficiently.

Figure 4:
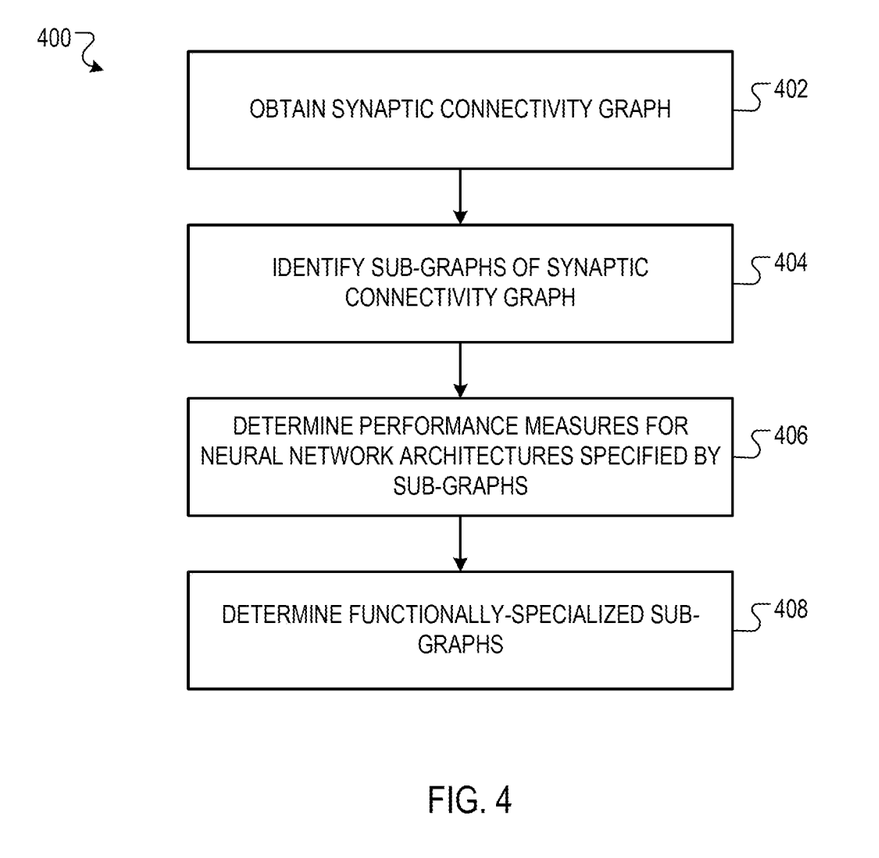
FIG. 4 is a flow diagram of an example process for performing neural functional localization by identifying regions of a brain that are predicted to be functionally-specialized for performing a task.

FIG. 4 is a flow diagram of an example process 400 for performing neural functional localization by identifying regions of a brain that are predicted to be functionally-specialized for performing a task. For convenience, the process 400 will be described as being performed by a system of one or more computers located in one or more locations. For example, a functional localization system, e.g., the functional localization system 200 of FIG. 2, appropriately programmed in accordance with this specification, can perform the process 400.

The system obtains data defining a synaptic connectivity graph representing synaptic connectivity between neurons in the brain of the biological organism (402).

The system identifies a set of sub-graphs of the synaptic connectivity graph (404).

The system determines, for each sub-graph, a performance measure characterizing a performance of a neural network having a neural network architecture that is specified by the sub-graph in accomplishing the task (406).

The system determines, based on the performance measures, that one or more of the sub-graphs correspond to regions of the brain of the biological organism that are predicted to be functionally-specialized for performing the task (408).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more data processing apparatus for identifying one or more regions of a brain of a biological organism that are predicted to be functionally-specialized for performing a task, the method comprising:
obtaining data defining a synaptic connectivity graph representing synaptic connectivity between neurons in the brain of the biological organism, wherein the synaptic connectivity graph is generated by processing a three-dimensional (3D) synaptic resolution image of the brain of the biological organism;
identifying a plurality of sub-graphs of the synaptic connectivity graph;
determining, for each sub-graph of the plurality of sub-graphs of the synaptic connectivity graph, a performance measure characterizing a performance of a neural network having a neural network architecture that is specified by the sub-graph of the synaptic connectivity graph in accomplishing the task, comprising, for each of the plurality of sub-graphs of the synaptic connectivity graph:
processing the sub-graph of the synaptic connectivity graph to generate a neural network having a neural network architecture that is specified by the sub-graph of the synaptic connectivity graph;
training the neural network having the neural network architecture that is specified by the sub-graph of the synaptic connectivity graph to accomplish the task; and
after the training, evaluating a performance measure of the neural network having the neural network architecture that is specified by the sub-graph of the synaptic connectivity graph in accomplishing the task; and
determining, based on the performance measures of neural networks having neural network architectures specified by the sub-graphs of the synaptic connectivity graph in accomplishing the task, that one or more sub-graphs of the plurality of sub-graphs of the synaptic connectivity graph correspond to regions of the brain of the biological organism that are predicted to be functionally-specialized for performing the task.

2. The method of claim 1, wherein the synaptic connectivity graph comprises a plurality of nodes and edges, wherein each edge connects a pair of nodes, each node corresponds to a respective neuron in the brain of the biological organism, and each edge connecting a pair of nodes in the synaptic connectivity graph corresponds to a synaptic connection between a pair of neurons in the brain of the biological organism.

3. The method of claim 2, wherein for each of the plurality of sub-graphs of the synaptic connectivity graph, processing the sub-graph of the synaptic connectivity graph to generate the neural network having the neural network architecture that is specified by the sub-graph of the synaptic connectivity graph comprises:
mapping each node in the sub-graph to a corresponding artificial neuron in the neural network architecture; and
for each edge in the sub-graph:
mapping the edge to a connection between a pair of artificial neurons in the neural network architecture that correspond to the pair of nodes in the sub-graph that are connected by the edge.

4. The method of claim 1, wherein identifying the plurality of sub-graphs of the synaptic connectivity graph comprises, at each of a plurality of iterations:
identifying a current sub-graph of the synaptic connectivity graph in accordance with current values of one or more parameters; and
updating the current values of the parameters based at least in part on the performance measure characterizing the performance of the neural network having the neural network architecture that is specified by the current sub-graph in accomplishing the task.

5. The method of claim 1, wherein evaluating the performance of the trained neural network having the neural network architecture that is specified by the sub-graph of the synaptic connectivity graph in accomplishing the task comprises:
determining an accuracy of the trained neural network having the neural network architecture in accomplishing the task.

6. The method of claim 1, wherein evaluating the performance of the trained neural network having the neural network architecture that is specified by the sub-graph of the synaptic connectivity graph in accomplishing the task further comprises:
determining a measure of complexity of the neural network architecture that is specified by the sub-graph of the synaptic connectivity graph.

7. The method of claim 1, further comprising:
providing data identifying the one or more sub-graphs of the plurality of sub-graphs corresponding to regions of the brain of the biological organism that are predicted to be functionally-specialized for performing the task.

8. The method of claim 1, further comprising:
generating a visualization of the one or more sub-graphs of the plurality of sub-graphs corresponding to regions of the brain of the biological organism that are predicted to be functionally-specialized for performing the task.

9. The method of claim 1, wherein the task is a visual data processing task.

10. The method of claim 1, wherein the task is an audio data processing task.

11. The method of claim 1, wherein obtaining data defining the synaptic connectivity graph representing synaptic connectivity between neurons in the brain of the biological organism comprises:
processing the 3D synaptic resolution image to segment: (i) a plurality of neurons in the 3D synaptic resolution image, and (ii) a plurality of synaptic connections between pairs of neurons in the 3D synaptic resolution image.

12. The method of claim 1, wherein the 3D synaptic resolution image of the brain of the biological organism is generated using electron microscopy techniques.

13. The method of claim 1, wherein determining, based on the performance measures of neural networks having architectures specified by sub-graphs of the synaptic connectivity graph in accomplishing the task, that one or more sub-graphs of the plurality of sub-graphs of the synaptic connectivity graph correspond to regions of the brain of the biological organism that are predicted to be functionally-specialized for performing the task comprises:
determining that a sub-graph of the synaptic connectivity graph associated with a highest performance measure corresponds to a region of the brain that is predicted to be functionally-specialized for performing the task.

14. A system comprising:
one or more computers; and
one or more storage devices communicatively coupled to the one or more computers, wherein the one or more storage devices store instructions that, when executed by the one or more computers, cause the one or more computers to perform operations for identifying one or more regions of a brain of a biological organism that are predicted to be functionally-specialized for performing a task, the operations comprising:
obtaining data defining a synaptic connectivity graph representing synaptic connectivity between neurons in the brain of the biological organism, wherein the synaptic connectivity graph is generated by processing a three-dimensional (3D) synaptic resolution image of the brain of the biological organism;
identifying a plurality of sub-graphs of the synaptic connectivity graph;
determining, for each sub-graph of the plurality of sub-graphs of the synaptic connectivity graph, a performance measure characterizing a performance of a neural network having a neural network architecture that is specified by the sub-graph of the synaptic connectivity graph in accomplishing the task, comprising, for each of the plurality of sub-graphs of the synaptic connectivity graph:
processing the sub-graph of the synaptic connectivity graph to generate a neural network having a neural network architecture that is specified by the sub-graph of the synaptic connectivity graph;
training the neural network having the neural network architecture that is specified by the sub-graph of the synaptic connectivity graph to accomplish the task; and
after the training, evaluating a performance measure of the neural network having the neural network architecture that is specified by the sub-graph of the synaptic connectivity graph in accomplishing the task; and
determining, based on the performance measures of neural networks having neural network architectures specified by the sub-graphs of the synaptic connectivity graph in accomplishing the task, that one or more sub-graphs of the plurality of sub-graphs of the synaptic connectivity graph correspond to regions of the brain of the biological organism that are predicted to be functionally-specialized for performing the task.

15. The system of claim 14, wherein the operations further comprise:
generating a visualization of the one or more sub-graphs of the plurality of sub-graphs corresponding to regions of the brain of the biological organism that are predicted to be functionally-specialized for performing the task.

16. The system of claim 14, wherein determining, based on the performance measures of neural networks having architectures specified by sub-graphs of the synaptic connectivity graph in accomplishing the task, that one or more sub-graphs of the plurality of sub-graphs of the synaptic connectivity graph correspond to regions of the brain of the biological organism that are predicted to be functionally-specialized for performing the task comprises:
determining that a sub-graph of the synaptic connectivity graph associated with a highest performance measure corresponds to a region of the brain that is predicted to be functionally-specialized for performing the task.

17. One or more non-transitory computer storage media storing instructions that when executed by one or more computers cause the one or more computers to perform operations for identifying one or more regions of a brain of a biological organism that are predicted to be functionally-specialized for performing a task, the operations comprising:
obtaining data defining a synaptic connectivity graph representing synaptic connectivity between neurons in the brain of the biological organism, wherein the synaptic connectivity graph is generated by processing a three-dimensional (3D) synaptic resolution image of the brain of the biological organism;
identifying a plurality of sub-graphs of the synaptic connectivity graph;
determining, for each sub-graph of the plurality of sub-graphs of the synaptic connectivity graph, a performance measure characterizing a performance of a neural network having a neural network architecture that is specified by the sub-graph of the synaptic connectivity graph in accomplishing the task, comprising, for each of the plurality of sub-graphs of the synaptic connectivity graph:
processing the sub-graph of the synaptic connectivity graph to generate a neural network having a neural network architecture that is specified by the sub-graph of the synaptic connectivity graph;
training the neural network having the neural network architecture that is specified by the sub-graph of the synaptic connectivity graph to accomplish the task; and
after the training, evaluating a performance measure of the neural network having the neural network architecture that is specified by the sub-graph of the synaptic connectivity graph in accomplishing the task; and
determining, based on the performance measures of neural networks having neural network architectures specified by the sub-graphs of the synaptic connectivity graph in accomplishing the task, that one or more sub-graphs of the plurality of sub-graphs of the synaptic connectivity graph correspond to regions of the brain of the biological organism that are predicted to be functionally-specialized for performing the task.

18. The non-transitory computer storage media of claim 17, wherein the operations further comprise:
generating a visualization of the one or more sub-graphs of the plurality of sub-graphs corresponding to regions of the brain of the biological organism that are predicted to be functionally-specialized for performing the task.

19. The non-transitory computer storage media of claim 17, wherein determining, based on the performance measures of neural networks having architectures specified by sub-graphs of the synaptic connectivity graph in accomplishing the task, that one or more sub-graphs of the plurality of sub-graphs of the synaptic connectivity graph correspond to regions of the brain of the biological organism that are predicted to be functionally-specialized for performing the task comprises:
determining that a sub-graph of the synaptic connectivity graph associated with a highest performance measure corresponds to a region of the brain that is predicted to be functionally-specialized for performing the task.

20. The non-transitory computer storage media of claim 17, wherein identifying the plurality of sub-graphs of the synaptic connectivity graph comprises, at each of a plurality of iterations:

identifying a current sub-graph of the synaptic connectivity graph in accordance with current values of one or more parameters; and updating the current values of the parameters based at least in part on the performance measure characterizing the performance of the neural network having the neural network architecture that is specified by the current sub-graph in accomplishing the task.

* * * * *